United States Patent [19]

Meriadec et al.

[11] 4,170,454

[45] Oct. 9, 1979

[54] PROCESS FOR THE PREPARATION OF A SOLID-PHASE RADIOIMMUNOASSAY SUPPORT AND USE THEREOF

[75] Inventors: Brigette Meriadec, La Grande Motte; Patrice Roubertie, Montpellier, both of France

[73] Assignee: Union Carbide Corporation, New York, N.Y.

[21] Appl. No.: 891,650

[22] Filed: Mar. 30, 1978

[51] Int. Cl.² .................. G01N 33/16; G01N 31/06
[52] U.S. Cl. ...................... 23/230.6; 23/230 B; 23/920; 424/1; 424/12; 435/7
[58] Field of Search ............ 23/230 B, 230.6; 195/63, DIG. 11; 424/1, 12

[56] References Cited

U.S. PATENT DOCUMENTS

| 3,659,104 | 4/1972 | Gross | 23/230.6 |
|---|---|---|---|
| 3,947,352 | 3/1976 | Cuatrecasas | 210/31 C |
| 3,953,172 | 4/1976 | Shapiro | 23/230 R |
| 3,961,894 | 6/1976 | Gordon | 23/230.6 |
| 3,970,429 | 7/1976 | Updike | 23/230.6 |
| 3,980,764 | 9/1976 | Adams | 424/1 |
| 3,996,162 | 12/1976 | McCall | 424/1 X |
| 4,018,883 | 4/1977 | Parslow | 424/1 |
| 4,055,493 | 10/1977 | Sawanishi | 210/31 C |
| 4,061,466 | 12/1977 | Gosta | 23/230.6 X |
| 4,070,348 | 1/1978 | Kraemer | 195/DIG. 11 |

OTHER PUBLICATIONS

M. Franek et al., J. Chromatog., 119, 167–172, (1976).
D. S. Skelly et al., Clin. Chem., 19 (2), 146–186, (1973).

Primary Examiner—Sidney Marantz
Attorney, Agent, or Firm—William Raymond Moran

[57] ABSTRACT

A solid-phase radioimmunoassay support, useful in chromatographic columns, is provided in tablet form which upon contact with an antigen-antibody solution swells to conform to the column configuration. The tablet is more easily handled, stored, and transported than the known wet, chromatographic columns presently in use.

7 Claims, No Drawings

PROCESS FOR THE PREPARATION OF A SOLID-PHASE RADIOIMMUNOASSAY SUPPORT AND USE THEREOF

This invention relates in general to a process for the preparation of a solid-phase radioimmunoassay support useful in chromatographic columns. In one aspect, this invention relates to a process for preparing a support in tablet form which upon contact with an antigen-antibody solution swells to conform to the column configuration. In a further aspect, this invention provides a support in tablet form which is easily transported, stored and used in automated clinical diagnostic methodologies.

The introduction of radioimmunoassay (RIA) in 1959 by Yalow and Berson[1] as a diagnostic tracer technique to replace the slow bioassay methods then in use has revolutionized many areas of clinical testing and research, owing to its specificity and extreme sensitivity.

[1]*Nature*, 184, 1648 (1959)

The RIA technique is based on the ability of an antibody and a specific antigen to form a reversible antigen-antibody complex. The assay is performed by adding a fixed quantity of radiolabeled antigen to samples which contain antiserum and known amounts of "standard" antigen. During incubation, radiolabeled antigen and unlabeled antigen compete for a limited number of binding sites on the antibody. After incubation, antibody-bound antigen is separated from the free antigen and the ratio of free to bound can be plotted on a dose-response curve. An unknown serum sample can then be assayed by the same procedure and the concentration of antigen determined by referring to the standard dose-response curve. Frequently, the classical methods of RIA are cumbersome, time consuming and have error-producing steps because of the requirements of multiple pipettings and test tubes, duplicate assays, prolonged incubation times and difficult, inefficient separation procedures.

Improvements in RIA have been directed most recently toward the use of solid-phase radioimmunoassay (SPRIA) and automation. For clarity in this disclosure, SPRIA refers to methods in which antiserum for a specific antigen is immobilized on or in a water-insoluble support, an immunosorbent, or a matrix for which the purpose of immobilization is to facilitate the separation of free antigen from immobilized antiserum-bound antigen.

As indicated, one area of improvements in radioimmunoassay is in the use of automated analytical devices. Such devices are currently in demand not only for radioimmunoassay but for other micro-analytical studies, such as those employed in biochemical research, routine clinical testing, enzymatic studies and the like.

Multistation analytical devices which utilize a centrifugal field have recently become available for the rapid microanalysis of a wide variety of liquids, such as body fluids, e.g., blood serum, food products and the like. For example, one such instrument which has been developed to automate radioimmunoassay is marketed by Union Carbide Corporation under the trademark "Centria". The Centria System offers several interesting features for performing solution phase immunoassays. The system consists of (a) an automated pipettor which dispenses samples and reagents, (b) the key module, an incubator/separator, in which centrifugal force is used to initiate and terminate multiple radioassay incubations and separations simultaneously, and (c) a gamma counter/computer which counts three tubes simultaneously and converts counts into concentration units. Further description and use of the Centria System is disclosed in U.S. Pat. No. 3,953,172 which issued Apr. 27, 1976, to S. I. Shapiro and G. Etingshausen and is assigned to the same assignee as this invention. As indicated in this patent, the system utilizes adsorption columns to separate the components to be analyzed. In the past, it was the accepted practice to purchase columns which already contained the appropriate adsorbent material and were ready for use without further preparation. While for the most part, such columns were satisfactory, they did not consistently meet the optimum requirements for clinical diagnostic techniques. When adsorption columns are utilized in devices which employ a centrifugal field, they must possess certain characteristics not ordinarily required for classical chromatographic methods which depend only on gravity flow. For instance, columns used in a centrifugal field may encounter column cracking or compaction due to loss of interstitial waters. Moreover, columns which have been prepared days or months prior to use may also encounter cracking, compaction and water loss during storage and transit.

It has now been found that the disadvantages noted for such columns can be avoided by the use of a solid-phase radioimmunoassay support which is provided in tablet form. The tablet is more easily handled, stored, transported and used than the known wet, chromatographic columns presently in use. The technician merely places a tablet in each column and upon contact with an antigen-antibody solution, the tablet swells to conform to the column configuration.

Accordingly, one or more of the following objects will be achieved by the practice of this invention. It is an object of this invention to provide radioimmunoassay supports which are useful in radioimmunoassay systems. Another object of this invention is to provide supports which are used in columns which are utilized in an analytical system which employs centrifugal force for mixing and transferring reactants. A further object of this invention is to provide supports in the form of tablet which can be safely stored until ready for use. Another object is to provide supports which swell within the columns to provide uniform gel substrates. A still further object is to provide a process for the preparation of the tablets of this invention. Another object is to provide a process of utilizing the tablets of this invention in radioimmunoassay. A still further object of this invention is to provide a solid-phase radioimmunoassay support comprised of a protein-bound gel of at least one antisera and a chromatographic gel. Another object is to provide, in tablet form, a protein-bound gel of Sepharose 4B and rabbit antibody antiserum. These and other objects will readily become apparent to those skilled in the art in the light of the teachings herein set forth.

In its broad aspect this invention is directed to a process for the preparation of a solid-phase radioimmunoassay support and its use thereof. The process comprises the steps of:

(a) contacting in the liquid phase to provide a protein-bound gel of (1) at least one antisera and (ii) a chromatographic gel capable of selectively retaining one or more components contained in an antigen-antibody-containing solution, (b) freeze-drying the protein-bound gel, (c) subdividing the dried gel to a powder, and
(d) forming the powder into a solid-phase support, such as a tablet.

Tablets prepared in accordance with the process of this invention have been found to be idealy suited for use in the chromatographic columns of the Centria System. As indicated in the examples, tablets can be prepared of a predetermined size and fluid capacity sufficient for the particular analysis being conducted. For example, tablets of 80 milligrams in weight and containing approximately 35 milligrams of the dried protein-bound gel were suitable for thyroid-stimulating hormone (TSH) radioimmunoassay test. The TSH test utilizes an immunological reaction in which labeled and unlabeled TSH molecules compete for binding sites on a specific antibody molecule. The Centria System utilizes centrifugal force to mix the different reagents at the same time on a special disc and after incubation to separate the bound and free antigen through the columns containing a second antibody on the solid-phase supports of this invention. The retaining means in the bottom of the column is of such a porosity and composition that all of the fluid transferred remains in the column for absorption by the tablet. Only upon increasing the centrifugal force above that required to transfer the fluids from the disc will liquid pass out of the column.

The process of the present invention is particularly useful for the preparation of chromatographic supports which are employed in second antibody solid-phase technology. It has been observed that many of the currently used gels, such as those marketed by Pharmacia under the tradename Sephadex G-25 and Sephadex A-50 encounter increasing difficulties when large molecular weight molecules are encountered. In contrast, it is believed that an advantage of the second-antibody solid-phase technology utilizing the supports of this invention is that there is no limit to the size of the antigen to which this technology may be applied. This is particularly true for supports prepared from Sepharose 4B, also marketed by Pharmacia.

The supports of this invention are not limited to the TSH RIA test but can be used with other antisera for a variety of analyses.

As previously indicated and as set forth in the examples, after gel preparation, the gel is bound to the appropriate antiserum and washed in accordance with accepted techniques. Thereafter the protein-bound gel is lyophilized by freeze-drying, subdivided and compressed into tablets.

It should be noted that while the tablets of this invention are particularly suited for use in systems which utilize a centrifugal field like the aforementioned Centria System, it, of course, is not limited to use in such devices. The advantages of easy storage, shipping and use also renders them idealy suited for chromatographic analyses which utilize gravity flow.

By the term "chromatographic gel" as employed throughout the specification and appended claims is meant the matrix or support which is capable of undergoing a multifold expansion by adsorption of fluid.

As previously indicated, the preferred supports prepared by the process of this invention are those comprised of Sepharose 4B, a commercially available cross-linked dextran product marketed by Pharmacia. Depending upon the desired swelling and retention characteristics, a variety of other carrier-type materials, such as Sephadex G-25 and A-50, agarose, marketed by Bi-orad, and the like, can also be processed in the solid-phase supports of this invention.

The following examples are illustrative:

EXAMPLE 1

Preparation of Solid-Phase Supports

This example sets forth the procedure for the preparation of a second antibody solid-phase support. Standard laboratory equipment and glassware (rinsed with 5N NaOH) were employed throughout. In each case, pharmaceutical grade reagents were employed.

(a) Buffer Solutions—For one liter of gel, the following buffers were employed in the support preparation. Their compositions are as follows:

| Buffer | Compositions | Quantity Prepared |
|---|---|---|
| A | $NaHCO_3$ 0.1M ph 8<br>33.6 g $NaHCO_3$/4 liters | 4 liters |
| B | $NaHCO_3$ 0.1M, NaCl 0.5M, ph 8<br>42 g $NaHCO_3$/5 liters<br>146.25 g NaCl/5 liters | 5 liters |
| C | $NaHCO_3$ 0.1M, $C_2H_7NO$ 1M, ph 9 | 3.5 liters |
|   | 29.4 g $NaHCO_3$<br>217 ml $C_2H_7NO$ 16.2M   /3.5 liters<br>~231 ml HCl32% | |
| D | $CH_3COONa$ 0.1M, NaCl 1M, ph 4 | 5 liters |
|   | 41 g $CH_3COONa$<br>292.3 g NaCl                /5 liters<br>~72 cc $CH_3COON$ | |
| E | Sodium borate 0.1M, NaCl 1M, ph 8 | 6 liters |
|   | 37.2 g $H_3BO_3$<br>350.7 g NaCl                /6 liters<br>~21 cc NaOH 10N (12g/30cc) | |
| F | Sodium phosphate 0.03M, $NaN_3$<br>0.02%, ph 7.5 | 4 liters |
|   | 3.18 g $NaH_2PO_4$<br>13.76 g $Na_2HPO_4$    /4 liters<br>0.8 g $NaN_3$ | |
| G | Same buffer + 0.2% BSA, 5% lactose, 1% dextran T10 | 400 ml |
|   | 400 ml Buffer F<br>+ 0.8 g BSA                  400 ml<br>+ 20 g lactose<br>+ 4 g dextran T10 | |

The carbonate buffers were prepared the morning of the day used whereas the other buffers were prepared the previous day.

(b) Gel Preparation—Cyanogen bromide (BrCN), 10 grams, is dissolved in 1 liter of distilled water in a 5 liter-beaker and thereafter is added one liter of a suspension of Sepharose[1]4B gel. The gel container is rinsed with 1 liter of distilled water which is then added to the mixture. Thereafter the pH is immediately adjusted to between 10.5 and 11.5 and maintained in this range for about 5 minutes by the dropwise addition of 5N NaOH (approximately 10 ml). The mixture containing the gel is immediately poured into a 3-liter Buchner funnel (3 porosity) and the solution withdrawn under vacuum. The gel is then washed in 5 liters of distilled water at +4° C. and thereafter 2.5 liters of Buffer A.

[1]Trademark of Pharmacia Gel (c) Binding Protein to Gel—The "cake" of gel is recovered with a spatula and placed in the bottom of a 5-liter beaker. The Buchner is rinsed with Buffer B and the antirabbit antibodies antiserum is added (the volume depends on the quality of the antiserum, e.g., Wellcome serum, 50 ml). The total volume of antiserum plus Buffer B is 500 ml. This provides 1 volume of gel +½ volume protein for binding. The binding is done by rotary agitation of a whisk at laboratory temperature over 4 hours.

When the binding is finished, the mixture is filtered in a Buchner. A fraction of the filtrate is kept at +4° C. for control. The gel is then washed with 1500 ml aliquots of each of the Buffers A, B and C. For each washing the mixture is agitated for 15 minutes and the liquid withdrawn before proceeding with the next washing. After the last washing the "cake" of gel is transferred to the bottom of a 5-liter beaker and the Buchner washed with 2 liters of Buffer C which are transferred to the beaker to provide 1 volume to gel and ½ volume of Buffer C. After agitation by rotation for 1 hour, the mixture is left to stand overnight. After standing overnight, the mixture is agitated for 15 minutes and the suspension poured into the Buchner and the liquid withdrawn. The gel is then rinsed and washed in accordance with the following sequence:

The gel is agitated 15 minutes with 1500 ml of Buffer A, and the liquid withdrawn.

Washing 1500 cc Buffer B, agitation 15 minutes withdrawal of liquid 1500 cc Buffer D agitation 15 minutes withdrawal of liquid 1500 cc Buffer E agitation 15 minutes withdrawal of liquid.

This washing cycle with Buffers D and E is performed 3 times.

1500 cc of Buffer E agitation 15 minutes withdrawal of liquid 1500 cc of Buffer F agitation 15 minutes withdrawal of liquid.

The gel is then reconstituted in a 1-liter beaker with 400 cc of Buffer G.

(d) Lyophilisation—The gel is transferred into two stainless steel trays, and then freeze-dried. Thereafter, the gel is tested to determine the weight necessary to recover 400 $\mu$l of incubation solution. This weight is then checked to ensure that it corresponds to the maximum binding capacity.

(e) Tablet Preparation—After lyophilisation of the gel has been completed, the solid is pulverized if necessary to provide a homogeneous product. The product is then sieved on a sieve having a porosity of 0.25 mm (Saulas et Cie., 16, Rue du Buisson St. Louis, 75010 Paris). Tablets such as 80 mg tablets are formulated blending approximately 35 mg of the sieved product, approximately 44 mg of dicalcium phosphate and 1 mg magnesium stearate, and pressing on a tabletting machine, (Frogerais type AM, 15, Rue de l'Yseu, 99440 Vitry/Seine) at 4000 kg/cm².

EXAMPLE 2

Clinical human blood serum samples were analyzed to determine the level of thyroid-stimulating hormone (TSH) therein using the Centria System marketed by Union Carbide Corporation. Samples of unknown TSH levels and standards solutions of known levels were processed simultaneously. This was accomplished by loading 20 cup positions with 250 microliters each of a particular clinical serum sample and 16 cup positions with 250 microliters of standard solutions. The standard TSH solutions employed contained 0.0 482 U/ml, 2.0 $\mu$U/ml, 4.0 $\mu$ml, 10 $\mu$U/ml, 20 $\mu$U/ml, 40 $\mu$/ml and 100 $\mu$/ml, respectively. The 125 I TSH was reconstituted with 5 ml of distilled water to give about 20,000 cpm per 50 $\mu$l. The TSH antiserum was reconstituted with 17 ml of distilled water and the NSB buffer reconstituted with 3 ml of distilled water.

The reagents and samples (50 $\mu$l) were pipetted automatically into the appropriate cavities of the transfer discs. The transfer disc is thereafter placed on the incubation separator module. After mixing of the reagents and samples, the mixture was allowed to incubate for 24 or 48 hours. After this incubation, the column ring was then loaded with test tubes and columns equipped with hydrophobic plugs in the incubator separator module. Into each column was placed a tablet prepared in accordance with the previous example. The mixture is transferred on the columns by using the centrifugal force. The tablet swells and the solid phase binds the whole antibody specific to the TSH. The solid phase is washed after 10 minutes of second incubation by approximately 2.5ml of a buffer solution (phosphate buffer 0.015 m, ph 7.5). The columns are thereafter measured on the third module of the centria and the measurements recorded from the computer.

Although the invention has been illustrated by the foregoing examples, it is not to be construed as being limited to the materials employed therein, but rather the invention encompasses the generic area as hereinbefore disclosed. Various modifications and embodiments of this invention can be made without departing from the spirit and scope thereof.

What is claimed is:

1. A process for the preparation of a solid-phase support useful in radioimmunoassay columns which support swells upon contact with an antigen-antibody-containing solution to conform to the shape of said columns, which process comprises the steps of:
    (a) contacting in the liquid phase to provide a protein-bound gel of (i) at least one antisera and (ii) a chromatographic gel said protein-bound gel capable of selectively retaining one or more components contained in an antigen-antibody-containing solution,
    (b) freeze-drying said protein-bound gel,
    (c) subdividing said dried gel to a powder, and
    (d) forming said powder into a solid-phase support.

2. The process of claim 1 wherein said powder is of a particle size sufficiently small to pass through a sieve having a porosity of 0.25 millimeters.

3. The process of claim 1 wherein said solid-phase support is in the form of a tablet.

4. The process of claim 1 wherein said solid-phase support is in the form of a tablet, said tablet being comprised of said dried protein-bound gel, dicalcium phosphate and magnesium stearate.

5. The process of claim 1 wherein said solid-phase support is in the form of a tablet and contains sufficient protein-bound gel to absorb at least 0.400 microliters of an antigen-antibody-containing solution.

6. A solid-phase support useful in radioimmunoassay columns, which support swells upon contact with an antigen-antibody-containing solution to conform to the shape of said columns, said support comprised of at least one antisera bound to a chromatographic gel and capable of selectively retaining one or more component contained in an antigen-antibody-containing solution.

7. In a radioimmunoassay wherein samples and reagents are mixed and transferred to chromatographic columns by means of centrifugal force, the improvement which comprises placing in said columns tablets prepared by the process of claim 1, and increasing said centrifugal force to an amount necessary to mix said samples and reagents and transfer them to the column containing said tablets, whereby said tablets swell and conform to the configuration of said columns.

* * * * *